(12) United States Patent
Schneerson et al.

(10) Patent No.: US 8,383,133 B2
(45) Date of Patent: Feb. 26, 2013

(54) **CONJUGATES OF *PLASMODIUM FALCIPARUM* SURFACE PROTEINS AS MALARIA VACCINES**

(75) Inventors: Rachel Schneerson, Bethesda, MD (US); Joanna Kubler-Kielb, Bethesda, MD (US); Yimin Wu, Frederick, MD (US); Louis Miller, Cabin John, MD (US); Fathy D. Majadly, Frederick, MD (US); John B. Robbins, New York, NY (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 349 days.

(21) Appl. No.: 12/444,963

(22) PCT Filed: Oct. 15, 2007

(86) PCT No.: PCT/US2007/081440
§ 371 (c)(1),
(2), (4) Date: Mar. 4, 2010

(87) PCT Pub. No.: WO2008/048945
PCT Pub. Date: Apr. 24, 2008

(65) Prior Publication Data
US 2010/0183678 A1 Jul. 22, 2010

Related U.S. Application Data

(60) Provisional application No. 60/851,961, filed on Oct. 16, 2006.

(51) Int. Cl.
*A61K 39/015* (2006.01)
*C07K 14/445* (2006.01)
(52) U.S. Cl. .................. 424/272.1; 424/268.1; 530/350

(58) Field of Classification Search .................. None
See application file for complete search history.

(56) References Cited

FOREIGN PATENT DOCUMENTS
| EP | 289110 | * | 1/1990 |
| WO | WO 98/14472 | | 4/1998 |
| WO | WO 99/29868 | | 6/1999 |

OTHER PUBLICATIONS

Kaslow et al 1988, Nature, 333 : 74-76.*
Reichlin et al 1970, JBC 245:947-954.*
Bernhard R. Beck et al Clin Infect Dis. 2003, 37 , 9 e126-e 128.*
Arakawa et al., "Nasal Immunization with a Malaria Transmission-Blocking Vaccine Candidate, Pfs25, Induces Complete Protective Immunity in Mice against Field Isolates of *Plasmodium falciparum*," *Infection and Immunity* 73(11):7375-7380, Nov. 2005.
Kubler-Kielb et al., "Additional Conjugation Methods and Immunogenicity of *Bacillus anthracis* Poly-γ-D-Glutamic Acid-Protein Conjugates," *Infection and Immunity* 74(8):4744-4749, Aug. 2006.
Kubler-Kielb et al., "Long-lasting and transmission-blocking activity of antibodies to *Plasmodium falciparum* elicited in mice by protein conjugates of Pfs25," *PNAS* 104(1):293-298, Jan. 2, 2007.
Qian et al., "Conjugating recombinant proteins to *Pseudomonas aeruginosa* ExoProtein A: a strategy for enhancing immunogenicity of malaria vaccine candidates," *Vaccine* 25(2):3923-3933, May 16, 2007.
International Search Report from International Application No. PCT/US2007/081440 dated Apr. 28, 2008.

* cited by examiner

*Primary Examiner* — Padma Baskar
(74) *Attorney, Agent, or Firm* — Klarquist Sparkman, LLP (57) ABSTRACT

Conjugates of ookinete surface protein Pfs25 are provided that are efficacious as vaccines against *Plasmodium falciparum*, the most severe form of malaria. Conjugates of ookinete surface protein Pvs25 for use as a vaccine against *Plasmodium vivax* are also provided. Methods for preparing the conjugates, which comprise the ookinete surface protein bound onto itself or onto another protein by a linking group, are also provided.

6 Claims, 2 Drawing Sheets

SEQUENCE LISTING

<160> NUMBER OF SEQ ID NOS: 2

<210> SEQ ID NO 1
<211> LENGTH: 187
<212> TYPE: PRT
<213> ORGANISM: Plasmodium vivax

<400> SEQUENCE: 1

```
Glu Ala Glu Ala Tyr Val Ala Val Thr Val Asp Thr Ile Cys Lys Asn
 1               5                  10                  15

Gly Gln Leu Val Gln Met Ser Asn His Phe Lys Cys Met Cys Asn Glu
            20                  25                  30

Gly Leu Val His Leu Ser Glu Asn Thr Cys Glu Glu Lys Asn Glu Cys
        35                  40                  45

Lys Lys Glu Thr Leu Gly Lys Ala Cys Gly Glu Phe Gly Gln Cys Ile
    50                  55                  60

Glu Asn Pro Asp Pro Ala Gln Val Asn Met Tyr Lys Cys Gly Cys Ile
65                  70                  75                  80

Glu Gly Tyr Thr Leu Lys Glu Asp Thr Cys Val Leu Asp Val Cys Gln
                85                  90                  95

Tyr Lys Asn Cys Gly Glu Ser Gly Glu Cys Ile Val Glu Tyr Leu Ser
            100                 105                 110
```

```
Glu Ile Gln Ser Ala Gly Cys Ser Cys Ala Ile Gly Lys Val Pro Asn
            115                 120                 125

Pro Glu Asp Glu Lys Lys Cys Thr Lys Thr Gly Glu Thr Ala Cys Gln
130                 135                 140

Leu Lys Cys Asn Thr Asp Asn Glu Val Cys Lys Asn Val Glu Gly Val
145                 150                 155                 160

Tyr Lys Cys Gln Cys Met Glu Gly Phe Thr Phe Asp Lys Glu Lys Asn
            165                 170                 175

Val Cys Leu Gly Pro His His His His His
            180                 185

<210> SEQ ID NO 2
<211> LENGTH: 185
<212> TYPE: PRT
<213> ORGANISM: Plasmodium falciparum

<400> SEQUENCE: 2

Glu Ala Glu Ala Tyr Val Lys Val Thr Val Asp Thr Val Cys Lys Arg
1               5                   10                  15

Gly Phe Leu Ile Gln Met Ser Gly His Leu Glu Cys Lys Cys Glu Asn
            20                  25                  30

Asp Leu Val Leu Val Asn Glu Glu Thr Cys Glu Glu Lys Val Leu Lys
            35                  40                  45

Cys Asp Glu Lys Thr Val Asn Lys Pro Cys Gly Asp Phe Ser Lys Cys
        50                  55                  60

Ile Lys Ile Asp Gly Asn Pro Val Ser Tyr Ala Cys Lys Cys Asn Leu
65                  70                  75                  80

Gly Tyr Asp Met Val Asn Asn Val Cys Ile Pro Asn Glu Cys Lys Gln
            85                  90                  95

Val Thr Cys Gly Asn Gly Lys Cys Ile Leu Asp Thr Ser Asn Pro Val
            100                 105                 110

Lys Thr Gly Val Cys Ser Cys Asn Ile Gly Lys Val Pro Asn Val Gln
            115                 120                 125

Asp Gln Asn Lys Cys Ser Arg Asp Gly Glu Thr Lys Cys Ser Leu Lys
130                 135                 140

Cys Leu Lys Glu Gln Glu Thr Cys Lys Ala Val Asp Gly Ile Tyr Lys
145                 150                 155                 160

Cys Asp Cys Lys Asp Gly Phe Ile Ile Asp Gln Glu Ser Ser Ile Cys
            165                 170                 175

Thr Asp Pro His His His His His
            180                 185
```

CONJUGATES OF *PLASMODIUM FALCIPARUM* SURFACE PROTEINS AS MALARIA VACCINES

CROSS REFERENCE TO RELATED APPLICATION

This application claims the benefit and priority to and is a U.S. National Phase of International Application Number PCT/US2007/081440, filed on Oct. 15, 2007, designating the United States of America and published in the English language, which is an International Application of and claims the benefit of priority to U.S. Provisional Patent Application No. 60/851,961, filed Oct. 16, 2006. The disclosures of the above-referenced applications are hereby expressly incorporated by reference in their entireties.

FIELD OF THE INVENTION

Conjugates of ookinete surface protein Pfs25 are provided that are efficacious as vaccines against *Plasmodium falciparum*, the cause of the most severe form of malaria. Conjugates of ookinete surface protein Pvs25 for use as a vaccine against *Plasmodium vivax* are also provided. Methods for preparing the conjugates, which comprise the ookinete surface protein bound onto itself or onto another protein by a linking group, are also provided.

DESCRIPTION OF THE RELATED ART

One approach for a vaccine against malaria is to block transmission of the parasite from mosquitoes to humans. When ingested by a mosquito with the blood meal, antibodies against the sexual, mosquito stage-specific surface antigens can block parasite development inside the vector (Carter, R. et al. 2000 *Nat Med* 6:241-244). Four proteins have been identified as potential inducers of transmission-blocking antibodies (Williamson, K. C. et al. 1993 *Mol Biochem Parasitol* 58:355-358; Carter, R. et al. 1990 *Parasite Immunol* 12:587-603; Kaslow, D C. et al. 1998 *Nature* 333:74-76; Duffy, P E. et al. 1993 *J Exp Med* 177:505-510). Two of these are expressed on the surface of gametes and in intracellular gameotocytes. The other two are the *Plasmodium falciparum* surface proteins with apparent molecular masses of 25 kDa (Pfs25) and 28 kDa (Pfs28), expressed exclusively on the zygote and ookinete surfaces during the mosquito stage of the infection. No antibody response to these two proteins has been shown in people infected with malaria and living in endemic countries (Carter, R. et al. 1989 *J Exp Med* 169:135-147). Pfs25 from different parts of the world has shown minimal variation in its amino acid sequence (Kaslow, D C. et al. 1989 *Mol Biochem Parasitol* 32:101-104). This relative homogeneity, likely a result from not being subjected to immune pressure in the human host, makes Pfs25 an attractive candidate for a malaria transmission-blocking vaccine (Barr, P J. et al. 1991 *J Exp Med* 174:1203-1208). However, Pfs25 is poorly immunogenic in mice and in humans, even if administered with adjuvant (Coban, C. et al. 2004 *Infect Immum* 72:584-588; Kaslow, D C. 2002 *Chem Immunol* 80:287-307). Increase in immunogenicity of protein-protein conjugates was obtained by others. Polymeric preparations of the cytochrome c were more immunogenic in animals than the corresponding monomeric proteins (Reichlin, M. et al. 1970 *J Biol Chem* 245:947-954), and an influenza hemagglutinin-diphtheria toxoid conjugate vaccine was more protective against influenza infection than the hemagglutinin alone (Gravenstein, S. et al. 1994 *J Am Geriat Soc* 42:245-251). Conjugates composed of the *Staphylococcus aureus* types: 5 and 8 capsular polysaccharides bound to carrier proteins by adipic acid dihydrazide or N-succinimidyl-3-(2-pyridyldithio)propionate have also been investigated, as well as other linking groups (Fattom, A. et al. 1992 *Infect Immun* 60:584-589; Kossaczka, Z. et al. 1999 *Infect Immun* 67:5806-5810, Schneerson et al J Exp Med 1980, 152:361-76). Antibody-mediated transmission blocking has been demonstrated for a human pathogen with an insect vector. Antibodies to *Borrelia burgdorferi* induced by the OspA vaccine were active in the gut of the *Ixodes* ticks (DeSilva, A M. et al. 1997 *Infect Immun* 65:3146-3150). The OspA protein was shown to be expressed mostly during the vector phase of the parasite, indicating that the transmission-blocking activity was induced by that vaccine.

SUMMARY OF THE INVENTION

An effective vaccine against malaria is highly desirable. Pfs25 bound onto itself or onto another protein induces high levels of transmission-blocking antibodies, indicating its efficacy as a vaccine against *Plasmodium falciparum*, the most severe form of the disease. A vaccine against *Plasmodium vivax* comprising Pvs25 bound onto itself or onto another protein is also provided.

Accordingly, in a first aspect, a conjugate is provided comprising a *Plasmodium falciparum* surface protein Pfs25 bound to an other protein via at least one linkage selected from the group consisting of an amide linkage, a hydrazone linkage, and a thioether linkage, wherein the conjugate is suitable for use as a malaria vaccine.

In an embodiment of the first aspect, the other protein is *Plasmodium falciparum* surface protein Pfs25.

In an embodiment of the first aspect, the other protein is *Pseudomonas aeruginosa* recombinant exoprotein A.

In an embodiment of the first aspect, the linkage is an amide linkage.

In an embodiment of the first aspect, the conjugate is of formula:

wherein n is an integer of from 3 to 5, $X_1$ is *Plasmodium falciparum* surface protein Pfs25, and $X_2$ is selected from the group consisting of *Pseudomonas aeruginosa* recombinant exoprotein A, ovalbumin, a *Plasmodium falciparum* surface protein Pfs25, tetanus toxoid, diphtheria toxoid, cholera toxin, *Clostridium difficile* toxin A, and *Clostridium difficile* toxin B. In a further embodiment, n is 4 and $X_2$ is *Pseudomonas aeruginosa* recombinant exoprotein A. In a further embodiment, n is 4 and $X_2$ is *Plasmodium falciparum* surface protein Pfs25.

In an embodiment of the first aspect, the linkage is a hydrazone linkage.
}

In an embodiment of the first aspect, the conjugate is of formula:

$$X_2\text{-NH-C(O)-}\underset{Z_1\ Z_2}{\overset{Z_3\ Z_4}{\text{Ar}}}\text{-CH=N-NH-C(O)-(CH}_2)_n\text{-C(O)-NH-NH-}X_1,$$

$$X_1\text{-NH-C(O)-}\underset{Z_1\ Z_2}{\overset{Z_3\ Z_4}{\text{Ar}}}\text{-CH=N-NH-C(O)-(CH}_2)_n\text{-C(O)-NH-NH-}X_2, \text{ or}$$

$$X_1\text{-NH-C(O)-}\underset{Z_1\ Z_2}{\overset{Z_3\ Z_4}{\text{Ar}}}\text{-CH=N-NH-C(O)-(CH}_2)_n\text{-C(O)-NH-N=CH-}\underset{Z_6\ Z_5}{\overset{Z_8\ Z_7}{\text{Ar}}}\text{-C(O)-NH-}X_2$$

wherein n is an integer of from 3 to 5, $X_1$ is *Plasmodium falciparum* surface protein Pfs25, $X_2$ is selected from the group consisting of *Pseudomonas aeruginosa* recombinant exoprotein A, ovalbumin, a *Plasmodium falciparum* surface protein Pfs25, tetanus toxoid, diphtheria toxoid, cholera toxin, *Clostridium difficile* toxin A, and *Clostridium difficile* toxin B, and wherein each of $Z_1$, $Z_2$, $Z_3$, $Z_4$, $Z_5$, $Z_6$, $Z_7$, and $Z_8$ is independently selected from the group consisting of hydrogen, halogen, and $C_{1-6}$ alkyl. In a further embodiment n is 4, $X_2$ is *Pseudomonas aeruginosa* recombinant exoprotein A, and wherein each of $Z_1$, $Z_2$, $Z_3$, $Z_4$, $Z_5$, $Z_6$, $Z_7$, and $Z_8$ is hydrogen. In a further embodiment, n is 4 and $X_2$ is *Plasmodium falciparum* surface protein Pfs25.

In an embodiment of the first aspect, the linkage is a thioether linkage.

In an embodiment of the first aspect, the conjugate is of formula:

$$X_1\text{-NH-C(O)-(CH}_2)_p\text{-NH-C(O)-(CH}_2)_r\text{-S-(CH}_2)_q\text{-C(O)-}X_2 \text{ or}$$

$$X_2\text{-NH-C(O)-(CH}_2)_p\text{-NH-C(O)-(CH}_2)_r\text{-S-(CH}_2)_q\text{-C(O)-}X_1$$

wherein p is an integer of from 1 to 3, q is an integer of from 1 to 3, r is 1 to 2, $X_1$ is *Plasmodium falciparum* surface protein Pfs25, and $X_2$ is selected from the group consisting of *Pseudomonas aeruginosa* recombinant exoprotein A, ovalbumin, a *Plasmodium falciparum* surface protein Pfs25, tetanus toxoid, diphtheria toxoid, cholera toxin, *Clostridium difficile* toxin A, and *Clostridium difficile* toxin B. In a further embodiment, p is 2, q is 2, r is 1, and $X_2$ is *Pseudomonas aeruginosa* recombinant exoprotein A. In a further embodiment, p is 2, q is 2, r is 1, and $X_2$ is *Plasmodium falciparum* surface protein Pfs25.

In a second aspect, a method for eliciting transmission-blocking activity of antibodies to *Plasmodium falciparum* in a host is provided, comprising administering the conjugate of the first aspect to the host.

In an embodiment of the second aspect, the host is a human.

In a third aspect, a pharmaceutical composition for eliciting transmission-blocking activity of antibodies to *Plasmodium falciparum* in a host is provided, the composition comprising a conjugate comprising *Plasmodium falciparum* surface protein Pfs25 bound to another protein via at least one linkage selected from the group consisting of an amide linkage, a hydrazone linkage, and a thioether linkage; and a pharmaceutically acceptable excipient.

In an embodiment of the third aspect, the composition further comprises an adjuvant, e.g., aluminum hydroxide.

In a fourth embodiment, a conjugate is provided comprising a *Plasmodium vivax* surface protein Pvs25 bound to an other protein via at least one linkage selected from the group consisting of an amide linkage, a hydrazone linkage, and a thioether linkage, wherein the conjugate is suitable for use as a malaria vaccine.

In an embodiment of the fourth aspect, the other protein is a *Plasmodium vivax* surface protein Pvs25.

In an embodiment of the fourth aspect, the other protein is *Pseudomonas aeruginosa* recombinant exoprotein A.

In an embodiment of the fourth aspect, the linkage is an amide linkage.

In an embodiment of the fourth aspect, the conjugate is of formula:

$$X_1\text{-NH-NH-C(O)-(CH}_2)_n\text{-C(O)-NH-NH-}X_2$$

wherein n is an integer of from 3 to 5, $X_1$ is *Plasmodium vivax* surface protein Pvs25, and $X_2$ is selected from the group consisting of *Pseudomonas aeruginosa* recombinant exoprotein A, ovalbumin, *Plasmodium vivax* surface protein Pvs25, Plasmodium falciparum surface protein Pvs25, tetanus toxoid, diphtheria toxoid, cholera toxin, Clostridium difficile toxin A, and Clostridium difficile toxin B. In a further embodiment, n is 24 and $X_2$ is Pseudomonas aeruginosa recombinant exoprotein A. In a further embodiment, n is 24 and $X_2$ is Plasmodium vivax surface protein Pvs25.

In an embodiment of the fourth aspect, the linkage is a hydrazone linkage.

In an embodiment of the fourth aspect, the conjugate is of formula:

$$X_2 \overset{H}{\underset{O}{N}} \overset{Z_3}{\underset{Z_1}{\overset{Z_4}{\underset{Z_2}{\text{Ar}}}}} \overset{O}{=} N \overset{H}{\underset{H}{N}} \overset{O}{=} (CH_2)_n \overset{O}{=} \overset{H}{\underset{H}{N}} \overset{H}{N} X_1,$$

$$X_1 \overset{H}{\underset{O}{N}} \overset{Z_3}{\underset{Z_1}{\overset{Z_4}{\underset{Z_2}{\text{Ar}}}}} = N \overset{H}{N} \overset{O}{=} (CH_2)_n \overset{O}{=} \overset{H}{N} \overset{H}{N} X_2, \text{ or}$$

$$X_1 \overset{H}{\underset{O}{N}} \overset{Z_3}{\underset{Z_1}{\overset{Z_4}{\underset{Z_2}{\text{Ar}}}}} = N \overset{H}{N} \overset{O}{=} (CH_2)_n \overset{O}{=} \overset{H}{N} N = \overset{Z_8}{\underset{Z_6}{\overset{Z_7}{\underset{Z_5}{\text{Ar}}}}} \overset{O}{=} \overset{H}{N} X_2$$

wherein n is an integer of from 3 to 5, $X_1$ is Plasmodium vivax surface protein Pvs25, $X_2$ is selected from the group consisting of Pseudomonas aeruginosa recombinant exoprotein A, ovalbumin, Plasmodium vivax surface protein Pvs25, Plasmodium falciparum surface protein Pvs25, tetanus toxoid, diphtheria toxoid, cholera toxin, Clostridium difficile toxin A, and Clostridium difficile toxin B, and wherein each of $Z_1$, $Z_2$, $Z_3$, $Z_4$, $Z_5$, $Z_6$, $Z_7$, and $Z_8$ is independently selected from the group consisting of hydrogen, halogen, and $C_{1-6}$ alkyl. In a further embodiment, n is 4, $X_2$ is Pseudomonas aeruginosa recombinant exoprotein A, and wherein each of $Z_1$, $Z_2$, $Z_3$, $Z_4$, $Z_5$, $Z_6$, $Z_7$, and $Z_8$ is hydrogen. In a further embodiment, n is 4 and $X_2$ is Plasmodium vivax surface protein Pvs25.

In an embodiment of the fourth aspect, the linkage is a thioether linkage.

In an embodiment of the fourth aspect, the conjugate is of formula:

$$X_1 \overset{H}{\underset{O}{N}} \overset{O}{=} (CH_2)_p \overset{H}{N} \overset{O}{=} (CH_2)_r - S - (CH_2)_q \overset{O}{=} \overset{H}{N} X_2 \text{ or}$$

$$X_2 \overset{H}{\underset{O}{N}} \overset{O}{=} (CH_2)_p \overset{H}{N} \overset{O}{=} (CH_2)_r - S - (CH_2)_q \overset{O}{=} \overset{H}{N} X_1$$

wherein p is an integer of from 1 to 3, q is an integer of from 1 to 3, r is 1 to 2, $X_1$ is Plasmodium vivax surface protein Pvs25, and $X_2$ is selected from the group consisting of Pseudomonas aeruginosa recombinant exoprotein A, ovalbumin, Plasmodium vivax surface protein Pvs25, Plasmodium falciparum surface protein Pvs25, tetanus toxoid, diphtheria toxoid, cholera toxin, Clostridium difficile toxin A, and Clostridium difficile toxin B. In a further embodiment, p is 2, q is 2, r is 1, and $X_2$ is Pseudomonas aeruginosa recombinant exoprotein A. In a further embodiment, p is 2, q is 2, r is 1, and $X_2$ is Plasmodium vivax surface protein Pvs25.

In a fifth aspect, a method for eliciting transmission-blocking activity of antibodies to Plasmodium vivax in a host is provided, comprising administering the conjugate of the fourth aspect to the host.

In an embodiment of the fifth aspect, the host is a human.

In an embodiment of the fifth aspect, the composition further comprises an adjuvant, e.g., aluminum hydroxide.

In a sixth aspect, pharmaceutical composition for eliciting transmission-blocking activity of antibodies to Plasmodium vivax in a host is provided, the composition comprising a conjugate comprising Plasmodium vivax surface protein Pvs25 bound to an other protein via at least one linkage selected from the group consisting of an amide linkage, a hydrazone linkage, and a thioether linkage; and a pharmaceutically acceptable excipient.

In a seventh aspect, use of the conjugate of the first or fourth aspect in the generation of sera as a reagent or for passive immunity is provided.

DETAILED DESCRIPTION OF THE PREFERRED EMBODIMENT

Malaria is a leading cause of morbidity and mortality, estimated to cause >1 million children deaths annually. *Plasmodium falciparum* causes the most severe form of the disease. There is as yet no licensed vaccine for this disease, despite over a half century of research. Conjugates of ookinete surface protein Pfs25 are provided that are efficacious as malaria transmission-blocking vaccines. Antibodies against Pfs25, drawn in during a bite, can block parasite development in the mosquito midgut, preventing transmission to other individuals. Pfs25 is a low-molecular-weight protein, by itself not immunogenic. To increase its immunogenicity, Pfs25 can be conjugated to itself or to other proteins, e.g., recombinant *Pseudomonas aeruginosa* exotoxin A, and ovalbumin, using amide, hydrazone, or thioether linkages. All conjugates were immunogenic and induced booster responses in mice. The scheme to form amide bonds between proteins by using adipic acid dihydrazide as a linker produced the most immunogenic conjugates, although other conjugates were also effective immunogenic agents. Adsorption of the conjugates onto aluminum hydroxide further increased the antibody levels. Surprisingly, the antibody levels 3 or 7 months after the last injection are significantly higher than those 1 wk after that injection. The observed transmission-blocking activity of immune sera correlated with antibody levels measured by ELISA.

Unless defined otherwise, technical and scientific terms used herein have the same meaning as commonly understood by one of ordinary skill in the art to which this invention belongs. See, e.g., Singleton P and Sainsbury D., *Dictionary of Microbiology and Molecular Biology* 3rd ed., J. Wiley & Sons, Chichester, N.Y., 2001. Further, unless otherwise required by context, singular terms shall include pluralities and plural terms shall include the singular.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

Pfs25 and Pvs25 Antigen

*Plasmodium falciparum* mosquito stage antigen Pfs25 and its homologue in *Plasmodium vivax, Pvs25*, are members of the P25 family of cysteine-rich 25 kDa antigens (see Kaslow et al, A vaccine Candidate from the Sexual Stage of Human Malaria that Contains EGF-like Domains, (1988) Nature 333: 74-76; Malkin et al., Phase 1 vaccine trial of Pvs25H: a transmission blocking vaccine for *Plasmodium vivax* malaria, (2005) Vaccine 23:3131-3138). They are composed of four tandem epidermal growth factor-like domains and are expressed on zygotes and mature ookinete stages of parasites within mosquitoes. Because P25 is only expressed in the mosquito midgut and not in the vertebrate host, these proteins have not been under selection pressure by the host immune system and antigenic variation of P25 appears to be more limited than most vaccine candidates present in pre-erythrocytic and asexual blood stages.

Linking Groups

The Pfs25 or Pvs25 antigen can be bonded to itself or to another protein via a suitable linking group. Particularly preferred linking groups include adipic acid dihydrazide (ADH), N-succinimidyl-4-formylbenzoate (SFB), N-succinimidyl-3-bromoacetamidopropionate (SBAP), and N-succinimidyl-3-(2-pyridyldithio)-propionate (SPDP):

Amide Linked Conjugates

Figure 1:
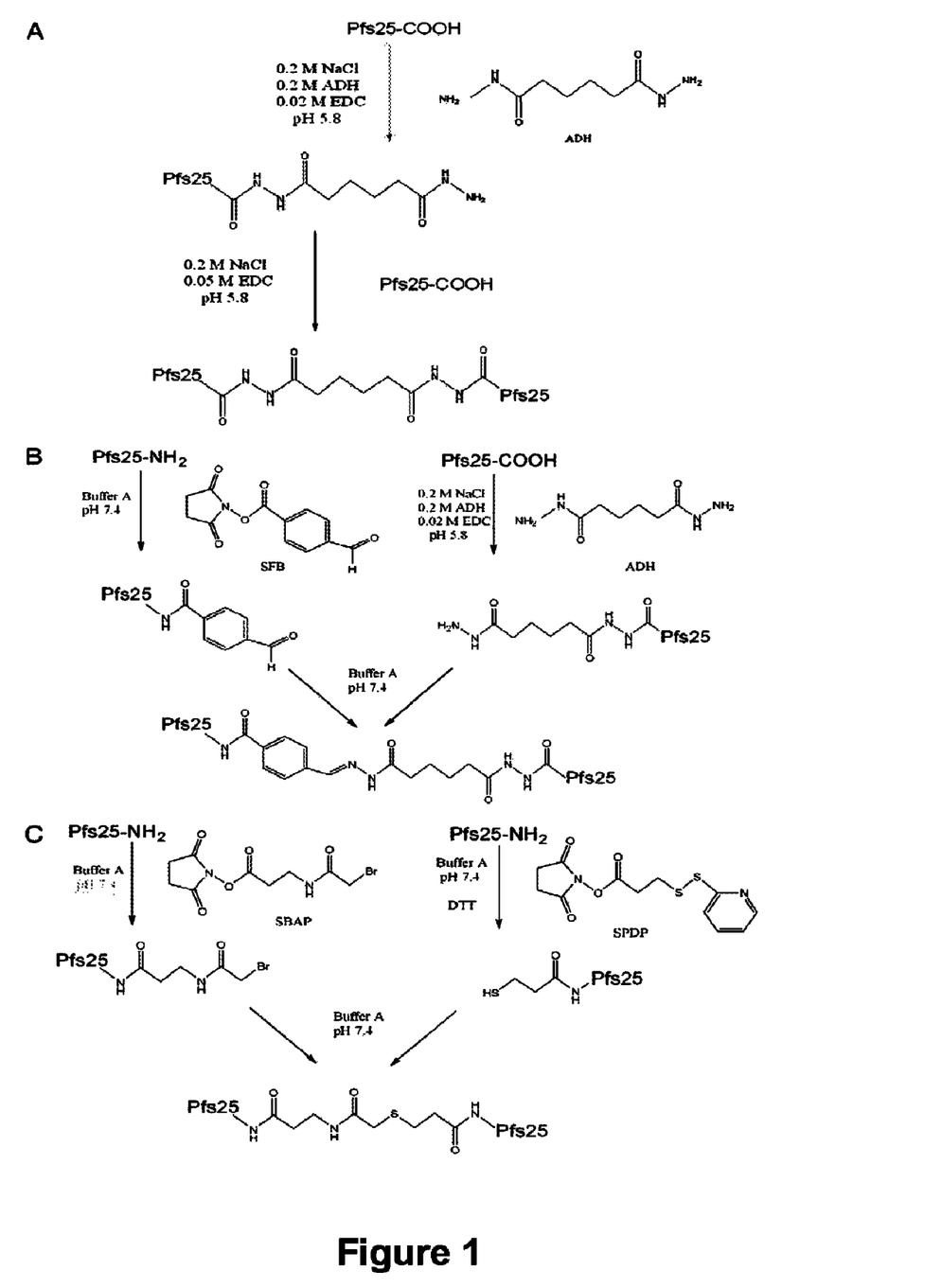
FIG. 1. Binding of Pfs25 to proteins by amide (A), hydrazone (B), or thioether linkages (C).

Adipic acid dihydrazide or a suitable analog, e.g., a member of the group of compounds of formula:

wherein n is 3 to 5, most preferably 4, can be employed as a linking agent yielding Pfs25 (or Pvs25) linked onto itself or onto another protein. A carboxylic acid moiety of the Pfs25 (or Pvs25) reacts with a hydrazide group of the linking agent to yield an amide linkage. FIG. 1A provides a schematic depicting the reaction of adipic acid dihydrazide with Pfs25 to yield a conjugate including multiple Pfs25 moieties covalently linked together. The reaction can advantageously be performed in two steps, as detailed in FIG. 1A, the first step involving derivatization of Pfs25 with the dihydrazide followed by a second step involving further reaction of the derivatized Pfs25 with additional unreacted Pfs25, or another protein (e.g., *Pseudomonas aeruginosa* recombinant exopro- tein A (rEPA), ovalbumin, Pvs25, tetanus toxoid, diphtheria toxoid, cholera toxin, *Clostridium difficile* toxin A or B or other protein carriers as are known in the art). Alternatively, the first step can involve derivatization of another protein, followed by further reaction of the derivatized protein with unreacted Pfs25. The conjugation reaction with Pfs25 (or Pvs25) can advantageously conducted according to the methods described in Schneerson et al. (1980) *J Exp Med* 152:361-376, the methods of the examples below, or other suitable methods, as will be appreciated by those of skill in the art. The resulting conjugates are of formula:

wherein n is as defined above, wherein $X_1$ is Pfs25 or Pvs25, and wherein $X_2$ is a protein such as Pfs25, Pvs25, rEPA, ovalbumin, or the like. Particularly preferred are compositions wherein n is 4 and wherein $X_1$ and $X_2$ are both Pfs25, or wherein $X_1$ and $X_2$ are both Pvs25, or wherein $X_1$ is Pfs25 and $X_2$ is Pvs25.

Hydrazone Linked Conjugates

Adipic acid dihydrazide, or a suitable analog such as described in the previous section, and N-succinimidyl-4-formylbenzoate or a suitable analog:

wherein each Z is independently hydrogen, halogen (e.g., F, Cl, Br, I), or lower alkyl (e.g., $C_{1-6}$ alkyl such as methyl, ethyl, etc.), preferably each Z is hydrogen, can be employed as linking agents to yield Pfs25 (or Pvs25) linked to itself or another protein via a hydrazone linkage. The reaction is preferably conducted in two steps, the first step involving two parts, as illustrated in FIG. 1B. In the first part of the first step, an amine moiety of Pfs25 (or Pvs25) reacts with N-succinimidyl-4-formylbenzoate or an analog thereof to yield a derivatized Pfs25 (or Pvs25). In the second part of the first step, a carboxylic acid moiety of Pfs25 (or Pvs25 or another protein) reacts with adipic acid dihydrazide or an analog thereof to yield derivatized Pfs25 (or Pvs25 or another protein). Alternatively, Pfs25 (or Pvs25) can be reacted to the adipic acid dihydrazide (or analog), and the other protein (or additional Pfs25 or Pvs25 respectively) can be reacted with the N-succinimidyl-4-formylbenzoate (or analog). The reaction of Pfs25 (or Pvs25) with N-succinimidyl-4-formylbenzoate can be advantageously conducted according to the methods of the examples below, or other suitable methods, as will be appreciated by those of skill in the art. In the second step, the two derivatives are reacted to yield a conjugate including a hydrazone linking group. The conjugate can be of formula:

or of formula:

wherein n, $Z_1$, $Z_2$, $Z_3$, $Z_4$, $X_1$ and $X_2$ are as defined above, depending upon which protein is reacted with N-succinimidyl-4-formylbenzoate (or analog thereof) and which protein is reacted with adipic acid dihydrazide (or analog). Particularly preferred are compositions wherein $Z_1$, $Z_2$, $Z_3$, $Z_4$ are each hydrogen, wherein n is 4 and wherein $X_1$ and $X_2$ are both Pfs25, or wherein $X_1$ and $X_2$ are both Pvs25, wherein $X_1$ is Pfs25 and $X_2$ is Pvs25, or wherein $X_1$ is Pvs25 and $X_2$ is Pfs25.

Alternatively, one of the derivatives of Pfs25 (or Pvs25) with N-succinimidyl-4-formylbenzoate (or analog) can be reacted with adipic acid dihydrazide (or analog), and the resulting derivative can then be reacted with a derivative of another protein with the N-succinimidyl-4-formylbenzoate (or analog), or more derivative of Pfs25 (or Pvs25) with N-succinimidyl-4-formylbenzoate (or analog). The resulting conjugate is of the formula:

wherein $Z_5$, $Z_6$, $Z_7$, and $Z_8$ are each independently hydrogen, halogen (e.g., F, Cl, Br, I), or lower alkyl (e.g., $C_{1-6}$ alkyl such as methyl, ethyl, etc.), preferably hydrogen, and wherein the remaining variables are as defined above. Particularly preferred conjugates are ones wherein each Z is hydrogen, wherein n is 4 and wherein $X_1$ and $X_2$ are both Pfs25, or wherein $X_1$ and $X_2$ are both Pvs25, or wherein $X_1$ is Pfs25 and $X_2$ is Pvs25.

Thioether Linked Conjugates

N-succinimidyl-3-bromoacetamidopropionate or a suitable analog:

wherein p is from 1 to 3, most preferably 2, wherein r is from 1 to 3, most preferably 1, and N-succinimidyl-3-(2-pyridyldithio)-propionate or a suitable analog:

wherein q is from 1 to 3, most preferably 2, can be employed as linking agents to yield Pfs25 (or Pvs25) linked to itself or another protein via a thioether linkage. The reaction is preferably conducted in two steps, the first step involving two parts, as illustrated in FIG. 1C. In the first part of the first step, an amine moiety of Pfs25 (or Pvs25) reacts with N-succinimidyl-3-bromoacetamidopropionate or an analog thereof to yield a derivatized Pfs25 (or Pvs25). In the second part of the first step, an amine moiety of Pfs25 (or Pvs25 or another protein) reacts with N-succinimidyl-3-(2-pyridyldithio)-propionate or an analog thereof to yield derivatized Pfs25 (or Pvs25 or another protein). Alternatively, Pfs25 (or Pvs25) can be reacted to the N-succinimidyl-3-(2-pyridyldithio)-propionate (or analog), and the other protein (or additional Pfs25 or Pvs25 respectively) can be reacted with the N-succinimidyl-3-bromoacetamidopropionate (or analog).

The reaction of Pfs25 (or Pvs25) with N-succinimidyl-3-bromoacetamidopropionate and N-succinimidyl-3-(2-pyridyldithio)-propionate can advantageously conducted according to the methods of the examples below, or other suitable methods, as will be appreciated by those of skill in the art. In the second step, the two derivatives are reacted to yield a conjugate including a thioether linking group. The resulting conjugates are of formula:

or formula:

wherein p, q, r, $X_1$ and $X_2$ are as defined above, depending upon which protein is reacted with N-succinimidyl-3-(2-pyridyldithio)-propionate (or analog thereof) and which protein is reacted with N-succinimidyl-3-bromoacetamidopropionate (or analog). Particularly preferred are compositions wherein p and q are each 2, wherein r is 1, and wherein $X_1$ and $X_2$ are both Pfs25, or wherein $X_1$ and $X_2$ are both Pvs25, wherein $X_1$ is Pfs25 and $X_2$ is Pvs25, or wherein $X_1$ is Pvs25 and $X_2$ is Pfs25.

Specific Binding Agents

Specific binding agents that can be bound to Pfs25 or Pvs25 can be used to form conjugates as disclosed herein. The binding agent can be used to purify and detect the Pfs25 or Pvs25. Examples of binding agents are polyclonal or monoclonal antibodies (including humanized monoclonal antibody), and fragments thereof, that can be bound to Pfs25 or Pvs25.

Monoclonal or polyclonal antibodies can be raised to recognize Pfs25 or Pvs25 conjugate, or an analog or derivative thereof. Substantially pure conjugate suitable for use as immunogen can be prepared as described above. Monoclonal or polyclonal antibodies to the conjugate can then be prepared.

Monoclonal antibodies to the polypeptides can be prepared from murine hybridomas according to the classic method of Kohler & Milstein (Nature 1975 256:495-97), or a derivative method thereof. Briefly, a mouse is repetitively inoculated with a few micrograms of the selected immunogen (for example, a Pfs25 or Pvs25 conjugate) over a period of a few weeks. The mouse is then sacrificed, and the antibody-producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as the enzyme-linked immunoabsorbent assay (ELISA), as originally described by Engvall (Meth. Enzymol. 1980, 70:419-39), or a derivative method thereof. Selected positive clones can be expanded and their monoclonal antibody product harvested for use. Detailed procedures for monoclonal antibody production are described in Harlow and Lane, Using Antibodies: A Laboratory Manual, CSHL, New York, 1999. Polyclonal antiserum containing antibodies can be prepared by immunizing suitable animals with an immunogen comprising a Pfs25 or Pvs25 conjugate.

Effective antibody production (whether monoclonal or polyclonal) is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (J Clin. Endocrinol. Metab., 1971, 33:988-91).

Booster injections can be given at regular intervals, and antiserum harvested when the antibody titer thereof, as determined semi-quantitatively, for example, by double immunodiffusion in agar against known concentrations of the antigen, begins to fall. See, for example, Ouchterlony et al., Handbook of Experimental Immunology, Wier, D. (ed.), Chapter 19, Blackwell, 1973. A plateau concentration of antibody is usually in the range of 0.1 to 0.2 mg/ml of serum (about 12 μM). Affinity of the antisera for the antigen is determined by preparing competitive binding curves, as described, for example, by Fisher (*Manual of Clinical Immunology*, 1980, Ch. 42).

Antibodies suitable for use can be contained in blood plasma, serum, hybridoma supernatants and the like. Alternatively, the antibodies can be isolated to the extent desired by well known techniques in the art, such as, ion exchange chromatography, sizing chromatography, or affinity chromatography. The antibodies can be purified so as to obtain specific classes or subclasses of antibody, such as IgM, IgG, IgA, IgG1, IgG2, IgG3, IgG4 and the like. Antibodies of the IgG class are of use for purposes of passive protection.

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz, *Methods Enzymol*. 1989 178:476-96; Glockshuber et al., *Biochemistry* 1990, 29:1362-67; and U.S. Pat. Nos. 5,648,237; 4,946,778; and 5,455,030. Conditions whereby a polypeptide/binding agent complex can form, as well as assays for the detection of the formation of a polypeptide/binding agent complex and quantitation of binding affinities of the binding agent and polypeptide, are standard in the art. Such assays can include, but are not limited to, Western blotting, immunoprecipitation, immunofluorescence, immunocytochemistry, immunohistochemistry, fluorescence activated cell sorting, fluorescence in situ hybridization, immunomagnetic assays, ELISA, ELISPOT (Coligan et al., Current Protocols in Immunology, Wiley, N.Y., 1995), agglutination assays, flocculation assays, cell panning, and the like, as are well known to one of skill in the art.

The antibodies or antibody fragments suitable for use have a number of diagnostic and therapeutic uses. For example, the antibodies or antibody fragments can be used for passive immunotherapy, such as by administering to a subject a therapeutically effective amount of the antibody or antibody fragments. In another example, the antibodies or antibody fragments can be used as in vitro diagnostic agents in various immunoassays to test for the presence of a microbe expressing Pfs25 or Pvs25 polypeptide in biological (for example, clinical) samples. Useful immunoassays include, but are not limited to, agglutination assays, radioimmunoassays, ELISA, fluorescence assays, Western blots and the like. In one such assay, for example, the biological sample is contacted first with an antibody which binds Pfs25 or Pvs25 polypeptide, and then with a labeled second antibody to detect the presence of a microbe, to which the first antibody has bound. Such assays can be, for example, of direct format (where a labeled first antibody is reactive with the Pfs25 or Pvs25 polypeptide), an indirect format (where a labeled second antibody is reactive with the first antibody), a competitive format (such as the addition of a labeled Pfs25 or Pvs25 polypeptide), or a sandwich format (where both labeled and unlabelled antibody are utilized), as well as other formats well known to one of skill in the art.

Binding agents of this disclosure can be bound to a substrate (for example, beads, tubes, slides, plates, nitrocellulose sheets, and the like) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $P^{32}$, $I^{125}$, $S^{35}$), an enzyme moiety (for example, horseradish peroxidase, alkaline phosphatase), a colloidal gold moiety, and a biotin moiety. Such conjugation techniques are standard in the art (for example, see Harlow and Lane, Using Antibodies: A Laboratory Manual, CSHL, New York 1999; Yang et al., *Nature* 1996 382:319-24).

Conjugate Products

Conjugates including only Pfs25 antigens, only Pvs25 antigens, or a mixture of Pfs25 and Pvs25 antigens are particularly preferred. However, conjugates of Pfs25 or Pvs25 and another protein can also be employed in the preparation of malaria vaccines. Suitable proteins include, but are not limited to, *Pseudomonas aeruginosa* recombinant exoprotein A and other proteins known in the art, as referred to elsewhere herein. Conjugates of Pfs25 or Pvs25 are preferred.

The highest antibody levels are generally obtained for conjugates having a molar ratio of Pfs25 or Pvs25 moieties to the other protein (which can also be Pfs25 or Pvs25, respectively) of greater than 1. The methods of preparing conjugates as described herein yield reaction products with a distribution of molecular weights. The resulting reaction mixture can be fractionated into fractions having different molecular weights. It is generally preferred to employ a conjugate having a molecular mass by SDS-PAGE of 50-250 kDa or greater.

A single type of conjugate can be employed, or a mixture of two or more conjugates can be employed.

Pfs25 (or Pvs25) conjugate can be used to generate sera as reagents or for passive immunity or for other such application known for the people in the art.

Pharmaceutical Compositions

In some embodiments, a conjugate of the preferred embodiments is in association with a pharmaceutically acceptable carrier. Compositions disclosed herein can be administered parenterally, or by any other suitable method for administering vaccines, as are known in the art. When administered systemically, the therapeutic composition is sterile, pyrogen-free and in a parenterally acceptable solution having due regard for pH, isotonicity, and stability. These conditions are known to those skilled in the art. Briefly, dosage formulations of the compounds described herein are prepared as solutions for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; amino acids such as glycine, glutamic acid, aspartic acid, or arginine; monosaccharides, disaccharides, and other carbohydrates including, glucose, mannose, or dextrans; chelating agents such as EDTA; sugar alcohols such as mannitol or sorbitol; counterions such as sodium and/or nonionic surfactants such as TWEEN, PLURONICS or polyethyleneglycol.

Sterile compositions for injection can be formulated according to conventional pharmaceutical practice as described in Remington: The Science and Practice of Pharmacy ($20^{th}$ ed, Lippincott Williams & Wilkens Publishers (2003)).

When the conjugate is administered by parenteral or other injection, it is preferably in the form of a pyrogen-free, parenterally acceptable aqueous solution. Suspensions can be formulated according to methods well known in the art using suitable dispersing or wetting agents and suspending agents. The preparation of acceptable aqueous solutions with suitable pH, isotonicity, stability, and the like, is within the skill in the art. A preferred pharmaceutical composition for injection preferably contains an isotonic vehicle such as sodium chloride or buffered sodium chloride solution. The pharmaceutical compositions can also contain stabilizers, preservatives, buffers, or other additives known to those of skill in the art.

The conjugate can be administered systematically or locally, via a liquid or gel, or as a device, e.g., a transdermal patch.

The conjugates of the preferred embodiments can additionally employ adjuvants conventionally found in pharmaceutical compositions in their art-established fashion and at their art-established levels. Thus, for example, the compositions can contain materials useful in physically formulating various dosage forms of the preferred embodiments. Adjuvants are commonly combined with vaccines for the purpose of improving immune response. Suitable adjuvants include aluminum hydroxide, phosphate or oxide, monophosphenyl lipid A, muramyl dipeptide, glucans, and Quil A. If aluminum hydroxide (alum) or aluminum phosphate is used, the amount used preferably complies with Code of Federal Regulation (CFR) and contains no more than 0.84 mg aluminum per dose.

The conjugate can be provided to an administering physician or other health care professional in the form of a kit. The kit is a package which houses one or more containers which contain conjugate in suitable form and instructions for administering the pharmaceutical composition to a subject. The kit can optionally also contain one or more additional therapeutic agents or adjuvants. The kit can optionally contain one or more diagnostic tools and instructions for use, e.g., a diagnostic to characterize a malarial infection. For example, a kit containing a single composition comprising conjugate in combination with one or more additional therapeutic agents can be provided, or separate pharmaceutical compositions containing conjugate and additional therapeutic agents can be provided. The kit can also contain separate doses of conjugate for serial or sequential administration. The kit can contain suitable delivery devices, e.g., syringes, and the like, along with instructions for administrating conjugate and any other therapeutic agent. The kit can optionally contain instructions for storage, reconstitution (if applicable), and administration of any or all therapeutic agents included. The kits can include a plurality of containers reflecting the number of administrations to be given to a subject.

EXAMPLES

Experimental Procedures

Analytic

Amino acid analyses were done by GLC-MS after hydrolysis with 6 N HCl at 150° C. for 1 h and derivatization to heptafluorobutyryl isobutyl esters and assayed with a Hewlett-Packard apparatus (Model HP 6890; Agilent Technologies, Wilmington, Del.) with a HP-5 0.32×30 mm glass capillary column, temperature programming at 8° C./min, from 125° C. to 250° C. in the electron ionization (106 eV) mode (MacKenzie, S L. 1987 *J Assoc Anal Chem* 70:151-160). Protein concentration was measured by the method of Lowry (Lowry, J O. et al. 1951 *J Biol Chem* 193:265-275); ratio of Pfs25 to carrier proteins was based on amino acid analysis of the conjugate and calculated as described (Shuler, K R. et al. 1992 *J Immunol Methods* 156:137-149). Free amino groups were measured by the Fields' assay (Fields, R. 1971 *Biochem J* 124:581-590); thiolation was measured by the release of 2-pyridylthio groups (A343) (Carlsson, J. et al. 1978 *Biochem J* 173:723-737); incorporation of benzaldehyde groups was measured by the reaction with 2-hydrazinopyridine (Kubler-Kielb, J. et al. 2006 *Infect Immun* 74:4744-4749); and hydrazide was measured by the trinitrobenzesulphonic acid (TNBS) assay (Schneerson, R. et al. 1980 *J Exp Med* 152:361-376). SDS/PAGE was performed using 14% gels according to the manufacturer's instructions. Double immunodiffusion was performed in 1.0% agarose gels in phosphate buffer solution (PBS).

Proteins

Recombinant Pfs25 expressed in *Pichia pastoris* and rEPA from *P. aeruginosa* were prepared and characterized as described (Tsai, C. et al. 2005 *J Biotechnol* 121:458:470; Johansson, H. et al. 1996 *J Biotechnol* 48:9-14). OVA was obtained from Sigma, St. Louis, Mo.

Immunization

Groups of 10 female NIH general purpose mice, 5- to 6-wk-old, were injected s.c. two or three times at 2-wk intervals with 2.5 µg of Pfs25 alone or as a conjugate in 0.1 ml of PBS. Mice were exsanguinated 1 wk after the last injection (Taylor, D N. et al. 1993 *Infect Immun* 61:3678-3687), or 1-9 months later. Controls received PBS. For the transmission-blocking assay, groups of 10 female BALB/c mice were injected s.c. two times, 4 wk apart, with 2.5 µg of Pfs25 as a conjugate formulated with aluminum hydroxide (Alhydrogel). Mice were exsanguinated 2 wk after the second injection.

Antibodies

Serum IgG antibodies were measured (see, e.g., Taylor et al., 1993, *Infect. And Immun.* 61:3678-87). Ninety-six-well plates (Nunc Maxisorb, Rochester, N.Y.) were coated with 4 µg of Pfs25/ml of PBS (determined by checkerboard titration). Plates were blocked with 0.5% BSA in PBS for 1 h at room temperature and incubated with test sera overnight, followed by phosphatase-labeled affinity-purified goat anti-mouse IgG (KPL, Gaithersburg, Md.) for 4 h. A MRX reader (Dynatech, Chantilly, Va.) was used to record the optical density. Antibody levels were calculated relative to a standard serum; a pool of sera with the highest antibody levels induced by Conjugate 1, containing 287 µg/ml antibodies. This concentration was assigned by comparison with affinity-purified IgG anti-Pfs25 of measured concentration. Results were computed with an ELISA data processing program provided by the Biostatistics and Information Management Branch, Centers for Disease Control, Atlanta, Ga. (Plikaytis, B D & Carlone, G M. 2005 *Program ELISA for Windows User's Manual* (Centers for Disease Control and Prevention, Atlanta,) Version 2). A polyclonal antiserum obtained by immunizing rabbits with Pfs25 formulated with Montanide ISA720 adjuvant (SEPPIC, Paris, France) was used in the immunodiffusion assays.

Conjugation of Pfs25 to Proteins by Amide Linkages

Pfs25-AH/Pfs25, Two-Step Procedure

Pfs25 was derivatized with ADH as described (Schneerson, R. et al. 1980 *J Exp Med* 152:361-376). The product, Pfs25-AH, contained 4.2-5.2% hydrazide. Next, equal amounts of Pfs25-AH and Pfs25 were mixed at 7.5 mg/ml each and reacted with 0.05 M 1-ethyl-3-[3-dimethylaminopropyl]carbodiimide hydrochloride (EDC) at pH 5.8 for 4 h at room temperature, tumbled overnight at 4-8° C., and dialyzed against PBS. This reaction mixture was then passed through a 1×90-cm Sepharose CL-6B column (Amersham Pharmacia, Pittsburgh, Pa.) in 0.2 M NaCl. Fractions reacting with anti-Pfs25 by immunodiffusion were divided into two pools according to their molecular masses, based on the column chromatography and SDS/PAGE profiles. Products: Conjugates 1 and 11 prepared by the same method at different times and containing the higher-molecular-mass fraction (F1); Conjugate 2 contained lower-molecular-mass fraction (F2) of Conjugate 1.

Pfs25-AH-Pfs25, One-Step Procedure

Pfs25 (15 mg/ml) was reacted with 0.006 M ADH (6% wt/wt) in the presence of 0.1 M EDC at pH 5.1 for 4 h at room temperature and tumbled overnight at 4-8° C. The reaction mixture was then treated as above. Products: Conjugates 12 and 13.

Pfs25-AH/rEPA

This conjugate was prepared in a two-step procedure as above, by using Pfs25-AH and rEPA at 10 mg/ml each. Products: Conjugates 14 and 15.

Conjugation of Pfs25 to Proteins by Hydrazone Linkages
Pfs25-AH/CHO-Pfs25

Pfs25 was derivatized with N-succinimidyl-4-formylbenzoate (Pfs25-CHO) and assayed for protein, benzaldehyde, and antigenicity as described (Kubler-Kielb, J. et al. 2006 *Infect Immun* 74:4744-4749). Pfs25-AH and Pfs25-CHO (10 mg each) were placed in 2 ml of Buffer A (PBS/0.1% glycerol/0.005 M EDTA, pH 7.4), reacted at pH 7.4 for 2 h, and then tumbled overnight at room temperature. The sample was then passed through a 1×90-cm Sepharose CL-6B column in Buffer A, and fractions reacting with anti-Pfs25 were assayed for protein concentration and molecular mass by SDS/PAGE. Products: Conjugates 6 and 8, prepared by the same method at different times.

Pfs25-CHO/AH-OVA

Derivatization of OVA to OVA-AH and Pfs25 to Pfs25-CHO and conjugation of these proteins was done as above. Products: Conjugates 5, 9, and 10.

Pfs25-AH-CHO-AH-Pfs25

Pfs25-AH was reacted with N-succinimidyl 4-formylbenzoate to introduce aldehyde groups onto the hydrazide groups as above for Pfs25-CHO. Pfs25-AH-CHO and Pfs25-AH (10 mg/ml each) were mixed in Buffer A at pH 7.4, tumbled overnight at 4-8° C., and passed through a Sepharose CL-6B column as above. Product: Conjugate 7.

Conjugation of Pfs25 to Proteins by Thioether Linkages
Pfs25-Br/SH-Pfs25

Pfs25 was derivatized with N-succinimidyl 3-(bromoacetamido) propionate and assayed for protein and antigenicity as described (Pfs25-Br) (Schneerson, R. et al. 2003 *PNAS USA* 100:8945-8950). Another aliquot of Pfs25 was derivatized with N-succinimidyl 3-(2-pyridyldithio)-propionate and assayed for protein, thiolation, and antigenicity (Pfs25-SH). Pfs25-Br and Pfs25-SH (10 mg of each) were placed in 2 ml of Buffer A and reacted at pH 7.4 for 2 h and then tumbled overnight at room temperature. The sample was then treated as above. Product: Conjugate 3.

Pfs25-SH/Br-OVA

Derivatization of OVA to OVA-Br and Pfs25 to Pfs25-SH and conjugation of these proteins was done as above. Product: Conjugate 4.

Transmission-Blocking Assay

Membrane feeding assay was performed as described (Quakyi, I. et al. 1987 *J Immunol* 139:4213-4217) to evaluate the transmission-blocking activity of the conjugate-induced antisera. Briefly, sera with the highest anti-Pfs25 levels from mice immunized with Conjugates 11 (Pfs25-AH/Pfs25) and 14 (Pfs25-AH/rEPA) formulated with Alhydrogel were each pooled and heat-inactivated at 56° C. for 15 min. The sera were then diluted serially with a naïve human serum pool to minimize nonspecific inhibitory effect of mouse sera. For each pool tested, a preimmune serum, diluted in parallel to the immune sera was used for baseline quantification of gametocyte. The diluted sera were mixed with a *P. falciparum* gametocyte culture (NF54 line) and fed to *Anopheles stephensi* (Nijmegen strain) through a membrane feeding apparatus. Mosquitoes were kept for 8 days to allow parasites to develop into mature oocysts. Infectivity was measured by dissecting at least 20 mosquitoes per serum sample, staining the midguts with mercurochrome (Sigma), and counting the number of oocysts per midgut. To calculate the percent inhibition, the following formula was used: $100 \times (\text{Oocyst\#}_{Neg\ control} - \text{Oocyst\#}_{Test})/\text{Oocyst\#}_{Neg\ control}$, where test and control sera were matched in serial dilution fold.

Characterization of Conjugates

Table 1 provides data as to serum IgG anti-Pfs25 elicited for conjugates of various compositions, including Pfs25 bound to itself, to *Pseudomonas aeruginosa* recombinant exoprotein A (rEPA), or to ovalbumin (OVA) by formation of amide (AH), hydrazone (AH/CHO, CHO/AH/CHO, or CHO/AH), or thioether (SH) linkages. Higher antibody levels were obtained with conjugates having a molar ratio of Pfs25 to carrier greater than 1 (compare, e.g., Example 14 to Example 15; Example 16 to Example 17; and Examples 5, 9, and 10 to each other). All conjugation methods increased the molecular mass of Pfs25, shown by the column elution profile and by SDS/PAGE, summarized in Table 1. Conjugates Pfs25-AH/Pfs25 (Conjugates 1 and 2), Pfs25-AH/rEPA (Conjugates 14 and 15), and Pfs25-CHO/AH-OVA (Conjugates 9 and 10) were heterogeneous in their molecular masses and were separated into two, partially overlapping fractions (F1 and F2). Conjugates that had estimated molecular masses >300 kDa were collected in only one fraction.

Derivatization of protein with adipic acid dihydrazide (ADH) was performed in two ways: (i) formation of amide bonds between carbodiimide activated aspartic and glutamic acid carboxyl groups of the proteins and the hydrazide of ADH (Conjugates 1, 2, and 11-15; FIG. 1A); (ii) formation of hydrazone linkages between benzaldehyde and hydrazide derivatized proteins (Conjugates 5-10; FIG. 1B). The longer linker, composed of an ADH molecule between two benzaldehyde molecules, was also prepared (Conjugate 7). Conjugates 3 and 4, containing thioether linkages between the two proteins, were also tested (FIG. 1C). All conjugates precipitated by double immunodiffusion with Pfs25 and carrier antibodies with an identity line, confirming the covalent binding of the two proteins and conservation of their antigenicity. Examples 11a-c were prepared the same way as conjugate 11, but at a different time to check for reproducibility. Results were reproducible since there was no statistical difference between conjugate 11 or conjugates 11a-c. Conjugates 16 and 17 were prepared as conjugate 15 but at different times; conjugates 18 and 19 were prepared as conjugate 12, but at different times. Conjugates 20 and 21 were prepared as conjugate 8.

TABLE 1

Composition and serum IgG anti-Pfs25 elicited by conjugates prepared by binding Pfs25 to itself, to rEPA, and to OVA

| Ex. | Conjugate | Molecular mass by SDS/PAGE, kDa | Pfs25/carrier, mol/mol | GM anti-Pfs25, µg/ml Second injection | GM anti-Pfs25, µg/ml Third injection |
|---|---|---|---|---|---|
|  | Pfs25 alone | 25 | na | nd | 0.05 |
|  | Pfs25 alone | 20 | na | nd | 0.05 |
| *Conjugation by amide linkages: two-step procedure* | | | | | |
| 1 | Pfs25-AH/Pfs25 F1 | 50-250 | na | nd | 352 |
| 2 | Pfs25-AH/Pfs25 F2 | 25-200 | na | nd | 98 |
| 11 | Pfs25-AH/Pfs25 F1 | 50-250 | na | nd | 296 |
| 11a | Pfs25-AH/Pfs25 F1 | 50-250 | na | 39 | 439 |
| 11b | Pfs25-AH/Pfs25 F1 | 50-250 | na | nd | 336 |
| 11c | Pfs25-AH/Pfs25 F1 (alum) | 50-250 | na | nd | 270 |
| 14 | Pfs25-AH/rEPA F1 | >300 | 1.8:1.0 | nd | 284 |
| 15 | Pfs25-AH/rEPA F2 | 100 to >300 | 2.5:1.0 | nd | 331 |
| 16 | Pfs25-AH/rEPA F1 | >300 | 1.8:1.0 | 150 | 593 |
| 17 | Pfs25-AH/rEPA F2 | 100 to >300 | 1.5:1.0 | nd | 367 |
| *Conjugation by amide linkages: one-step procedure* | | | | | |
| 12 | Pfs25-AH-Pfs25 F1 | 50-200 | na | nd | 150 |
| 13 | Pfs25-AH-Pfs25 F2 | 25-100 | na | nd | 11 |
| 18 | Pfs25-AH-Pfs25 | 50-200 | na | nd | 239 |
| 19 | Pfs25-AH-Pfs25 | 50-200 | na | 10 | 354 |
| *Conjugation by thioether linkages* | | | | | |
| 3 | Pfs25-Br/SH-Pfs25 | 50 to >300 | na | nd | 88 |
| 4 | Pfs25-SH/Br-OVA | >300 | 0.6:1.0 | 0.4 | 24 |
| *Conjugation by hydrazone linkages* | | | | | |
| 6 | Pfs25-AH/CHO-Pfs25 | >300 | na | 5.0 | 36 |
| 8 | Pfs25-AH/CHO-Pfs25 | >300 | na | 4.5 | 71 |
| 20 | Pfs25-AH/CHO-Pfs25 F1 | >300 | na | nd | 329 |
| 21 | Pfs25-AH/CHO-Pfs25 F2 | 100 to >300 | na | nd | 301 |
| 7 | Pfs25-CHO/AH/CHO-Pfs25 | >300 | na | 0.005 | 17 |
| 5 | Pfs25-CHO/AH-OVA | >300 | 0.3:1.0 | 0.02 | 12 |
| 9 | Pfs25-CHO/AH-OVA F1 | >300 | 2.0:1.0 | 17 | 69 |
| 10 | Pfs25-CHO/AH-OVA F2 | >300 | 4.4:1.0 | 24 | 123 |

Five- to 6-wk-old NIH general purpose mice (n = 10) injected s.c. with 2.5 µg of Pfs25 as conjugate 2 wk apart and exsanguinated 7 d after the second or third injection.

Statistics:
1 vs. 2, P = 0.002;
1 vs. 12, P = 0.008;
11 vs. 2, P = 0.03;
12 vs. 13, P = 0.003;
3 vs. 4, P = 0.05;
8 vs. 7, P = 0.02;
1 vs. 3, P = 0.02;
1 vs. 8, P = 0.001.
na, not applicable;
nd, not done.

Immunogenicity of Conjugates

The antibody levels induced by all conjugates after three injections were significantly higher than those induced by Pfs25 alone (Table 1; P<0.001). The most immunogenic conjugates were Pfs25 bound to itself by ADH (geometric mean (GM) 439 µg/ml) or to rEPA (GM 593 µg/ml) in a two-step reaction. Conjugates prepared with ADH induced statistically higher antibody levels than similar conjugates prepared with thioether (352 vs. 88 µg/ml; P=0.02) or hydrazone linkages (352 vs. 71 µg/ml; P=0.001). The Pfs25 linked to itself by a two-step procedure was more immunogenic than by a one-step procedure (P=0.008). The conjugate containing longer linker (Conjugate 7), with ADH separated from the protein by benzaldehyde rings, produced significantly lower antibody levels compared with levels induced by Conjugates 1 and 12, where only ADH served as the linker. When the method was adjusted to avoid too much cross-linking, similar levels were achieved, e.g., 329 µg/ml in the case of Conjugate 20, wherein only ADH served as a linker.

Carrier Effect

Conjugates of Pfs25 linked to rEPA via ADH induced antibody levels similar to those induced by Pfs25 linked to itself by the same method. Conjugates prepared by linking Pfs25 to OVA by thioether linkages induced significantly lower antibody levels than Pfs25 bound to itself by the same method (24 vs. 88 µg/ml; P=0.05). Conjugate of Pfs25 bound to itself (Conjugate 3) and to OVA (Conjugate 4) by hydrazone linkages elicited similar levels of anti-Pfs25 but significantly lower than those prepared with ADH (71 vs. 352 µg/ml; P=0.001).

Size Effect

The immunogenicity of the conjugates was not directly related to their sizes. To be immunogenic, conjugates of Pfs25 onto itself and onto other proteins had at least 2 equivalents of Pfs25. Conjugates prepared by the same method with molecular masses between 100 and 300 kDa (Conjugate 14) and >300 kDa (Conjugate 15) induced similar levels of antibodies (Table 1).

Dosage Effect

Two dosages of several Pfs25 conjugates were tested in mice (Table 2). There were no statistically significant differences in the antibody levels between the dosage of 2.5 and 10 µg per mouse per injection.

TABLE 2

Dosage/immunogenicity relation of conjugates of Pfs25 bound to itself or to OVA.

| | | | GM anti-Pfs25, µg/ml | |
|---|---|---|---|---|
| No. | Conjugate | Dosage, µg per mouse | Second injection | Third injection |
| 1 | Pfs25-AH/Pfs25 | 2.5 | nd | 352 |
| 1 | Pfs25-AH/Pfs25 | 10 | nd | 311 |
| 2 | Pfs25-AH/Pfs25 | 2.5 | nd | 98 |
| 2 | Pfs25-AH/Pfs25 | 10 | nd | 161 |
| 3 | Pfs25-Br/SH-Pfs25 | 2.5 | nd | 88 |
| 3 | Pfs25-Br/SH-Pfs25 | 10 | nd | 76 |
| 4 | Pfs25-Br/SH-Pfs25 | 2.5 | 0.15 | 24 |
| 4 | Pfs25-Br/SH-Pfs25 | 10 | 0.3 | 72 |
| 5 | Pfs25-AH/CHO-Pfs25 | 2.5 | 0.007 | 12 |
| 5 | Pfs25-AH/CHO-Pfs25 | 10 | 1.2 | 32 |

Five- to 6-wk-old NIH general purpose mice (n = 10) were injected s.c. with 2.5 or 10 µg of Pfs25 as conjugate, 2 wk apart and exsanguinated 7 d after the second or third injection.
nd, not done.

TABLE 3

Serum IgG anti-Pfs25 elicited at different times after immunization by 2.5 µg of conjugate per mouse

| | | Time of bleeding | GM anti-Pfs25, µg/ml | |
|---|---|---|---|---|
| No. | Conjugate | after last injection | Second injection | Third injection |
| 6 | Pfs25-AH/CHO-Pfs25 | 1 wk | 5 | 36 |
| 6 | Pfs25-AH/CHO-Pfs25 | 7 mo | 96 | 142 |
| 12 | Pfs25-AH-Pfs25 F1 | 1 wk | 5 | nd |
| 12 | Pfs25-AH-Pfs25 F1 | 3 mo | 247 | nd |

Five- to 6-wk-old NIH general purpose mice (n = 10) were injected s.c. with 2.5 µg of Pfs25 as conjugate 2 wk apart and exsanguinated 7 d, 3 mo, or 7 mo after the second or third injection.
nd, not done.

Statistics: 5 vs. 96, P = 0.0005;

36 vs. 142, P = 0.03;

5 vs. 247, P = 0.002.

A vaccine based on Pfs25 has unusual properties, in that with the passage of time, the level of antibodies increases, as demonstrated in the data of Table 4. A maximum level of antibodies was achieved at 3 months in this experiment.

TABLE 4

Antibody levels versus time for Pfs25 vaccines

| | | | | Time of bleeding | ELISA anti-Pfs25, µg/ml | |
|---|---|---|---|---|---|---|
| No. | Conjugate | Protein concentration | Pfs Concentration | after last injection | Second injection | Third injection |
| 2 | Pfs-AH/Pfs | | 50 µg/ml | 1 week | 39 | 439 |
| 2 | Pfs-AH/Pfs | | | 1 month | 89 | 574 |
| 3 | Pfs-AH/Pfs | | | 2 months | 229 | |
| 3 | Pfs-AH/Pfs | | | 3 months | 314 | 826 |
| 3 | Pfs-AH/Pfs | | | 9 months | 150 | 225 |
| 3 | Pfs-AH/Pfs on alum | | 25 µg/ml | 1 week | 239 | |
| 3 | Pfs-AH/Pfs on alum | | | 3 months | 1174 | |
| 3 | Pfs-AH/Pfs on alum | | | 9 months | 314 | |
| 16 | rEPA-AH/Pfs | 520 µg/ml | | 1 week | 150 | |
| 16 | rEPA-AH/Pfs | | | 1 month | 210 | |
| 16 | rEPA-AH/Pfs | | | 2 months | 280 | |
| 16 | rEPA-AH/Pfs | | | 3 months | 203 | |
| 16 | rEPA-AH/Pfs | | | 9 months | 129 | |

Duration of Pfs25 Conjugates-Induced Antibodies

Remarkably, the levels of antibodies of mice bled 3 or 7 months after the last injection were significantly higher than those obtained 1 wk after the last injection (Table 3; 96 vs. 5 µg/ml; P=0.0005; 142 vs. 36 µg/ml; P=0.03; 247 vs. 5 µg/ml; P=0.002).

Conjugates-Induced Mouse Anti-Pfs25 Exerted Transmission-Blocking Activity

Figure 2:
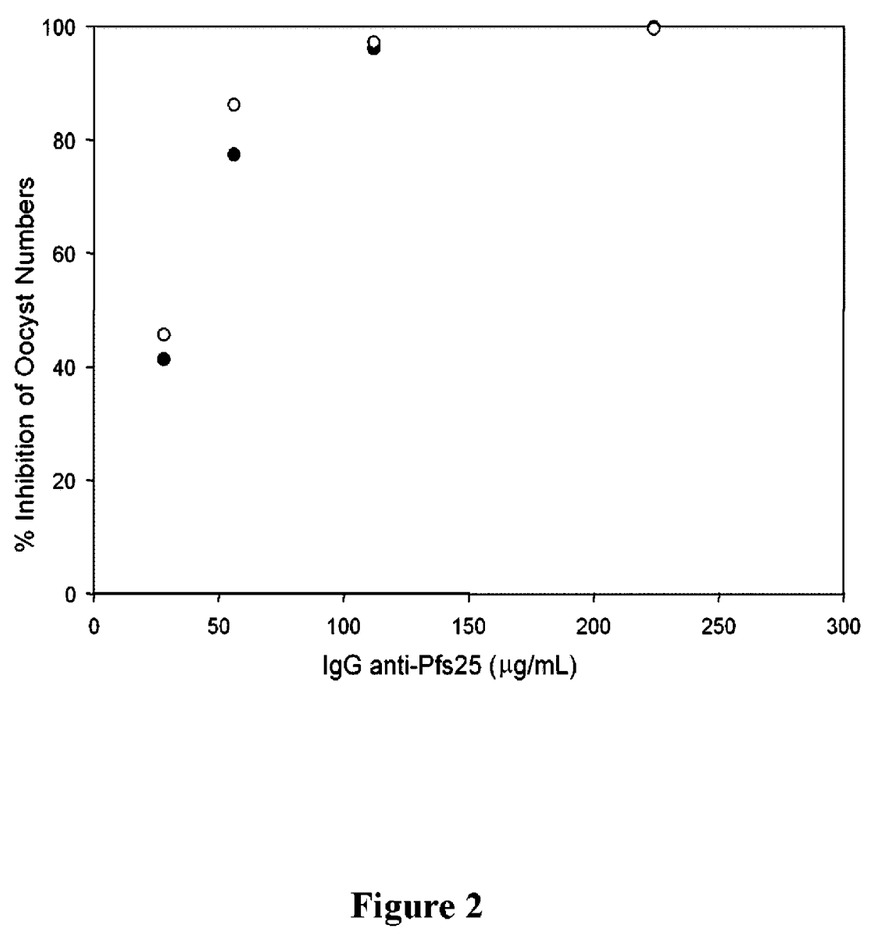
FIG. 2. Percent inhibition of oocyst numbers as a function of IgG anti-Pfs25 concentration (μg/mL) indicates that conjugates-induced transmission-blocking activity correlates with the specific IgG concentration in the assay. Two groups of mice were immunized with Pfs25-AH/Pfs25 F1 on Alhydrogel (filled circles) or rEPA/AH-Pfs25H F1 on Alhydrogel (open circles) on days 0 and 28. Antisera were obtained 2 wk after the second immunization and diluted with a naïve human serum pool to reach the desired antibody concentration. The diluted antisera and parasites were fed to mosquitoes, and the oocyst numbers in mosquito midguts were counted as an indication of the infectivity.

Transmission-blocking assay was performed by using pooled sera of mice injected with Conjugates 11 (Pfs25-AH/Pfs25 F1) and 14 (rEPA/AH-Pfs25 F1) formulated with Alhydrogel. Sera from naïve mice were used to calculate the percent inhibition of oocyst count. Both pools showed significant transmission-blocking activity, demonstrated by reduction of oocyst numbers in mosquito midgut (FIG. 2). This activity correlated with serum antibody levels measured by ELISA.

Adsorption onto Aluminum Hydroxide Enhances the Immunogenicity of the Conjugates After the third injection, Conjugate 14 induced a GM of 284 µg/ml, compared with the adsorbed Conjugate 14 that induced a GM of 1,445 µg/ml (P<0.001). Similarly, Conjugate 11 alone induced a GM of 296 µg/ml, and the adsorbed Conjugate 11 induced a GM of 2,125 µg/ml (P<0.001).

Results

The *P. falciparum* surface protein Pfs25 is expressed only on the ookinetes in the midgut of the mosquito vector. It is not encountered by the human host, and therefore human antibody response to it cannot be expected, even in endemic areas. Antibodies elicited by immunization of experimental animals with Pfs25 plus adjuvant inhibit the malarial parasite development in mosquitoes (Barr, P J. et al. 1991 *J Exp Med* 174:1203-1208). Alone or adsorbed onto aluminum hydroxide, Pfs25 is poorly immunogenic in experimental animals and in humans (Coban, C. et al. 2004 *Infect Immun* 72:584-588; Kaslow, D C. 2002 *Chem Immunol* 80:287-307). Accordingly, a method is provided to increase the immunogenicity of the Pfs25 by conjugation. The methods of preferred embodiments are reproducible and can be clinically used, including in infants. A particularly preferred linking agent is ADH, which provided the most immunogenic Pfs25 conjugates.

Two variables, the conjugation method and the conjugate composition, were examined for Pfs25 conjugates prepared with the ADH linker. First, the two-step procedure, derivatization of Pfs25 with ADH, followed by binding of the Pfs25-AH to nonderivatized Pfs25, resulted in more immunogenic conjugates than the one-step method. Second, the immunogenicity of conjugates prepared with rEPA or of Pfs25 linked to itself was similar. However, the simplest scheme for production and standardization renders the Pfs25 linked to itself particularly preferred.

Conjugates of Pfs25 composed of 2-10 molecules (as indicated by a molecular weight of 50-250 kDa) are particularly preferred immunogens. Increasing the dosage of Pfs25 conjugates from 2.5 to 10.0 µg per injection did not affect the antibody levels; accordingly, lower dosage levels may confer acceptable antibody levels. Adsorption of the Pfs25 conjugates onto aluminum hydroxide enhanced their immunogenicity. Conjugate-induced transmission-blocking activity correlated to antibody levels measured by ELISA, indicating the conjugates to be suitable for use as a malaria vaccine.

Surprisingly, rather than declining, the levels of Pfs25 antibodies rose 3 and 7 months after the second and third injections, relative to levels obtained after 1 wk. In a second study (see data in Table 4), the level of antibodies reached a peak at 3 months after injection, with a slow decline at 9 months after the last injection. Pfs25 as a conjugate, bound to itself or to another protein, showed a significant increase in immunogenicity compared to Pfs25 alone.

*Plasmodium vivax* ookinete surface protein, Pvs25, an orthologue of Pfs25, was found to be safe and immunogenic and elicited transmission-blocking antibodies in adult humans when adsorbed onto aluminum hydroxide (Malkin, E M. et al. 2005 *Vaccine* 23:3131-3138); however, it was believed that the vaccine-induced levels of anti-Pvs25H were too low for an effective vaccine and that natural boosting of these levels could not be expected because the antigen was not expressed on the parasite in its human host. The conjugation methods as disclosed herein can be employed with Pvs25 to improve its immunogenicity so as to yield conjugates suitable for use as vaccines against *Plasmodium vivax*.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. A conjugate comprising a first protein that comprises a *Plasmodium falciparum* surface protein Pfs25 bound to a second protein that comprises a *Plasmodium falciparum* surface protein Pfs25, wherein the conjugate having the formula $$X_1-\underset{H}{N}-\underset{H}{N}-\underset{O}{\overset{H}{C}}-(CH_2)_n-\underset{O}{\overset{O}{C}}-\underset{H}{N}-\underset{H}{N}-X_2$$

wherein n is an integer of from 3 to 5, $X_1$, is a *Plasmodium falciparum* surface protein Pfs25 and $X_2$ is a *Plasmodium falciparum* surface protein Pfs25, wherein the conjugate has a molecular weight of 50 to 250 kDa.

2. The conjugate of claim 1, wherein n is 4.

3. A pharmaceutical composition for eliciting transmission-blocking activity of antibodies to a *Plasmodium* in a host, comprising:
   a conjugate of claim 1; and
   a pharmaceutically acceptable excipient.

4. The pharmaceutical composition of claim 3, further comprising an adjuvant.

5. The pharmaceutical composition of claim 3, wherein the adjuvant is aluminum hydroxide.

6. A method of inducing an immune response to a Malaria antigen in a mammal comprising:
   providing the conjugate of claim 1 to said mammal; and
   measuring the immune response of said mammal.

* * * * *